United States Patent [19]

Liotta

[11] 4,446,232
[45] May 1, 1984

[54] ENZYME IMMUNOASSAY WITH TWO-ZONED DEVICE HAVING BOUND ANTIGENS

[76] Inventor: Lance A. Liotta, 5621 Sonoma Rd., Bethesda, Md. 20817

[21] Appl. No.: 310,801

[22] Filed: Oct. 13, 1981

[51] Int. Cl.³ .................. G01N 33/54; G01N 33/58; G01N 33/52; G01N 33/76
[52] U.S. Cl. ........................ 435/7; 422/56; 435/805; 436/514; 436/515; 436/529; 436/530; 436/531; 436/535; 436/810; 436/818; 436/820
[58] Field of Search ............. 435/4, 7, 188, 810, 435/805; 422/55, 56, 57, 58, 61; 436/514, 515, 518, 528, 529, 530, 531, 532, 535, 63, 516

[56] References Cited

U.S. PATENT DOCUMENTS

| | | | |
|---|---|---|---|
| 3,654,090 | 4/1972 | Schuurs et al. | 195/103.5 |
| 3,723,064 | 3/1973 | Liotta | 23/230 |
| 3,791,932 | 2/1974 | Schuurs et al. | 195/103.5 |
| 3,926,732 | 12/1975 | Rosen et al. | 435/805 |
| 3,981,981 | 9/1976 | Reunner et al. | 436/530 |
| 3,992,158 | 11/1976 | Przybylowicz et al. | 23/253 |
| 4,016,043 | 4/1977 | Schuurs et al. | 195/103.5 |
| 4,042,335 | 8/1977 | Clement | 23/253 |
| 4,059,407 | 11/1977 | Hochstrasser | 435/7 |
| 4,066,403 | 1/1978 | Bruschi | 23/230 |
| 4,094,647 | 6/1978 | Deutsch et al. | 435/7 |
| 4,168,146 | 9/1979 | Grubb et al. | 422/56 |
| 4,181,501 | 1/1980 | Keese et al. | 23/230 |
| 4,200,436 | 4/1980 | Mochida et al. | 23/230 |
| 4,200,690 | 4/1980 | Root et al. | 435/7 |
| 4,248,829 | 2/1981 | Kitajima et al. | 435/805 |
| 4,258,001 | 3/1981 | Pierce et al. | 422/56 |
| 4,264,560 | 4/1981 | Natelson | 422/58 |
| 4,277,560 | 7/1981 | Gray et al. | 435/7 |

OTHER PUBLICATIONS

Patonetto, F.—Proc. Soc. Exp. Biol. Med. 113: 394–397, 1963, The Fluorescent Antibody Technique Applied to Titration and Identification of Antigens in Solution or Antisera.
Nakane, P. K. and Pierce, G. B.—J. Histochem. Cytochem. 14: 929–931, 1966, Enzyme Labeled Antibodies: Preparation and Application for Localization of Antigens.
Avrameas, S. and Uriel, J.—CR Acad. Sci. 262: 2543–2545, 1966, Methode de Marguage D'Antigenes et D'Anticorps avec des Enzymes et Son Application en Immunodifussion.
Miles, L. E. M. and Hales, C. N.—Nature (London) 219: 186–189, 1968, Labelled Antibodies and Immunologic Assay Systems.
Cuatrecasas, P.—J. Biol. Chem. 245: 3059–3065, 1970, Protein Purification by Affinity Chromatography.
Engvall, E. and Perlmann, P.—Immunochemistry 8: 871–874, 1971, Enzyme Linked Immunosorbent Assay (Elisa), Quantitative Assay of Immunoglobulin G.
Avrameas, S. and Builbert, B.—Comp. Rend. Acad. Sci. Paris D273: 2705–2707, 1971, Dosage Enzymo-Immunologique de Proteines a L'Aide D'Immunoadsorbants et D'Antigens Marques aux Enzymes.
Uotila, M., Ruoslahti, E., and Engvall E.-J. of Immunol. Meth. 42, 11–15, 1981, Two Site Sandwich Immunoassay with Monoclonal Antibodies to Human Alpha-Fetoprotein.

*Primary Examiner*—Sidney Marantz
*Attorney, Agent, or Firm*—Fay & Sharpe

[57] ABSTRACT

A device for determining the presence of antigens which comprises a first zone containing antigens and enzyme-linked antibodies which are capable of immunologically reacting with said antigens, said antibodies being positioned in said first zone such that they will be removed from said first zone when reacted with antigens passing through said first zone but not removed from said first zone in the absence of such antigens, and a second zone containing material capable of reacting with said enzyme-linked antibodies to produce a color forming reaction which indicates the presence of said antibodies.

23 Claims, 6 Drawing Figures

ENZYME IMMUNOASSAY WITH TWO-ZONED DEVICE HAVING BOUND ANTIGENS

BACKGROUND OF THE INVENTION

The present invention relates to a device and method for determining the presence of antigens in biological fluids.

Immunologic diagnostic tests are widely used for the detection of body fluid antigens, hormones, infectious agents, and serum antibodies. Immunoassays generally fall into the following two categories. First, antibody-antigen precipitation tests, such as radial immunodiffusion, hemagglutination, and coated latex particle agglutination. Second, labeled-reagent tests, such as radioimmunoassay, and enzyme-linked immunoassay.

The precipitation type tests have the advantage of being performed manually and are commercially used in disposable kits which are read visually and do not require an instrument. The reading from a precipitation type immunoassay is usually expressed as the presence or absence of an agglutination reaction at each of a series of known dilutions of the test sample or competing antigen. The disadvantages of the precipitation type tests is that they are much less sensitive than the labeled reagent assays, require time consuming incubation steps, and are susceptible to subjective error in visual identification of a precipitation reaction.

Labeled reagent immunoassays are quantitative and highly sensitive but, nevertheless, have certain disadvantages. Radioimmunoassays employ radioactive tracers and, therefore, require a gamma radiation detection instrument. The radioactive tracers have a short shelf life, pose a health hazard to the technician and have been subject to restrictive legislation. Enzyme-linked immunoabsorbant assays (ELISA) use reagents labeled with an enzyme. The enzyme is detected by its reaction with a substrate to yield a product that can be easily measured (for example by formation of a color). The ELISA does not require radioactive materials and uses reagents with a long shelf life.

The ELISA assay beings with the binding of a reference reagent to a solid phase support, such as the bottom of a plastic well. Test fluid, mixed with enzyme-labeled reagent, is reacted with the bound reference reagent. Through a number of dilution, incubation and washing steps (as many as fourteen), bound and free reagents are separated, and a color forming reaction is initiated. The intensity of the color formed at different serial dilutions provides the quantitative measure. The standard ELISA takes between four and twelve hours to perform. Consequently, the major disadvantage of the ELISA is the large number of dilution, incubation, and washing steps, which are time consuming and subject to error.

The device of the present invention is used to overcome many of the difficulties associated with the above-discussed type of assay. Specifically, the use thereof results in an improved ELISA which requires no dilution, no washing steps, and one short incubation period. The assay is in the form of a dry, layered test strip which forms a color reaction when exposed directly to the test fluid. The strip automatically performs the dilution steps required for quantitation and separates the bound antibody from the free antibody. The color reaction can be read visually, or with an instrument, such as a spectrophotometer. In addition, the device of the present invention can be fabricated in strip form and employed as a dipstick for rapidly detecting an antigen, such as a drug or hormone in urine. An example of a specific application would be the rapid detection of a drug overdose in the Emergency Room, or as a home pregnancy test.

SUMMARY OF THE INVENTION

In one aspect, the present invention concerns a device for determining the presence of antigens which comprises a first zone containing antigens and enzyme-linked antibodies which are capable of immunologically reacting with said antigens, said antibodies being positioned in said first zone such that they will be removed from said first zone when reacted with antigens passing through said first zone but not removed from said first zone in the absence of such antigens, and a second zone containing material capable of reacting with said enzyme-linked antibodies to produce a color forming reaction which indicates the presence of said antibodies.

In another aspect, the instant invention is directed to a unique method for determining the presence of antigens in a biological fluid which comprises bringing said fluid into contact with a device of matrix having a first zone containing antigens and enzyme-linked antibodies which are capable of immunologically reacting with said antigens, said antibodies being positioned in said first zone such that they will be removed from said first zone when reacted with antigens passing through said first zone but not removed from said first zone in the absence of such antigens, and a second zone containing material capable of reacting with said enzyme-linked antibodies to produce a color forming reaction which indicates the presence of said antibodies; allowing said fluid to permeate said device or matrix; and observing the presence or absence of any color change in said second zone to thereby determine the presence or absence of the tested for antigen in said fluid.

Figure 6:
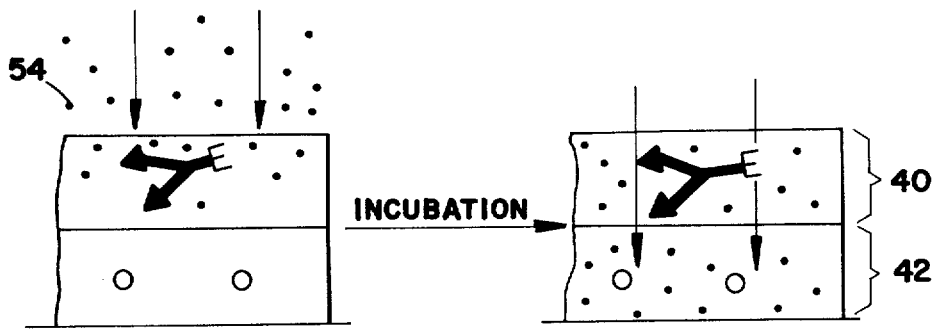

Conversely, as shown in FIG. 6, when the test fluid 54 is devoid of antigen, no competition will take place, and consequently no enzyme-linked antibody will diffuse into second zone 42 and no color will be produced.

DESCRIPTION OF THE PRACTICE OF THE INVENTION

The present invention is based on the principle of competition between bound and free antigens for a fixed number of recognition sites on an enzyme-labeled antibody. It is an improved method for performing the ELISA type test. The reagents of the assay are impregnated into a multi-zoned test strip. The liquid sample to be tested is allowed to passively diffuse into the test strip. Bound and free antigens are automatically separated during the diffusion. This separation is accomplished by having the solid phase reference antigen immobilized in a first zone which is separate from a secone zone containing the enzyme substrate. Soluble enzyme-linked antibody, which has recognition sites, is allowed to mix with the test sample and diffuse through the layers. The soluble antigens in the test sample compete with the immobilized reference antigen for combining with the enzyme-linked antibody. Therefore, the amount of enzyme-linked antibody which ultimately reaches the second zone containing the substrate, depends on the concentration of the antigen being tested in the sample. The substrate in the test strip reacts with the enzyme to produce a color reaction.

In order to provide quantitation the test strip is constructed with multiple, separate regions, each containing a different amount of immobilized reference antigen. The position of the color change on the test strip is, therefore, dependent on the concentration of the antigen in the test sample.

As hereinbefore noted, the device of the present invention includes a first zone which contains bound antigen and specific enzyme-linked antibody and a second zone which contains a color forming reagent or substrate. The enzyme-linked antibodies are positioned in the first zone in such a manner that they are capable of being removed from the first zone when reacted with unbounded antigen entering or passing therethrough but not removed from the first zone in the absence of such antigens.

Figure 1:
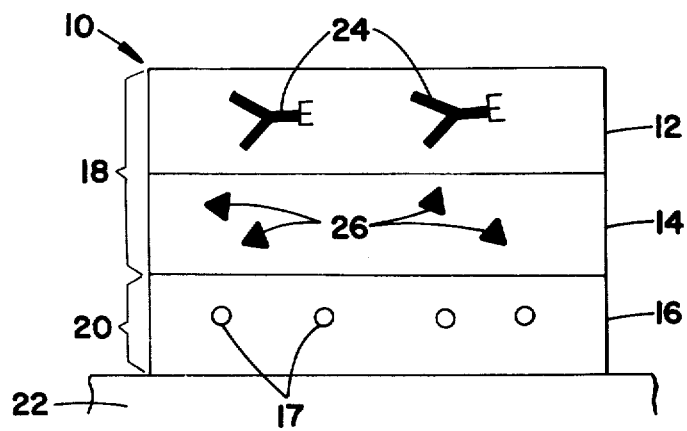
FIG. 1 is a diagrammatical illustration of the device 10 of the present invention which is constructed in three distinct layers, 12, 14 and 16. Layers 12 and 14 form the first zone 18. Layer 16 forms the second zone 20. The device 10 is shown positioned on a supporting member 22. Layer 12 is fashioned from a porous material which has dispersed therein soluble enzyme-linked antibodies 24. Layer 14 is also formed from a porous material and has bound thereto antigens 26. Layer 16, likewise, is fabricated from a porous material and contains a bound color-forming reagent 17, i.e., a material which reacts with an enzyme to produce a color.
Figure 2:
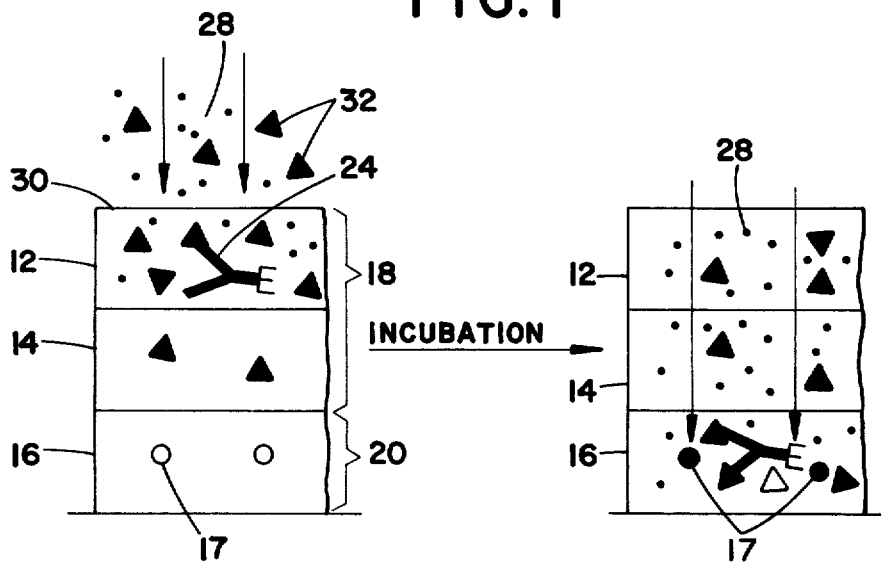
FIG. 2 is a diagrammatical illustration showing the method of the invention using the device of FIG. 1. Specifically, a fluid, generally identified by the numeral 28, is applied to the surface 30 of layer 12. As the fluid diffuses through the matrix, free antigen 32 contacts and combines with enzyme-linked antibodies 24. After a short incubation period, the enzyme-linked antibodies with saturated recognition sites freely diffuse through first zone 18 and into the second zone 20 (or layer 16) where the enzyme reacts with the color forming reagent to produce a distinctive color which indicates the presence of antigen in the applied fluid.
Figure 3:
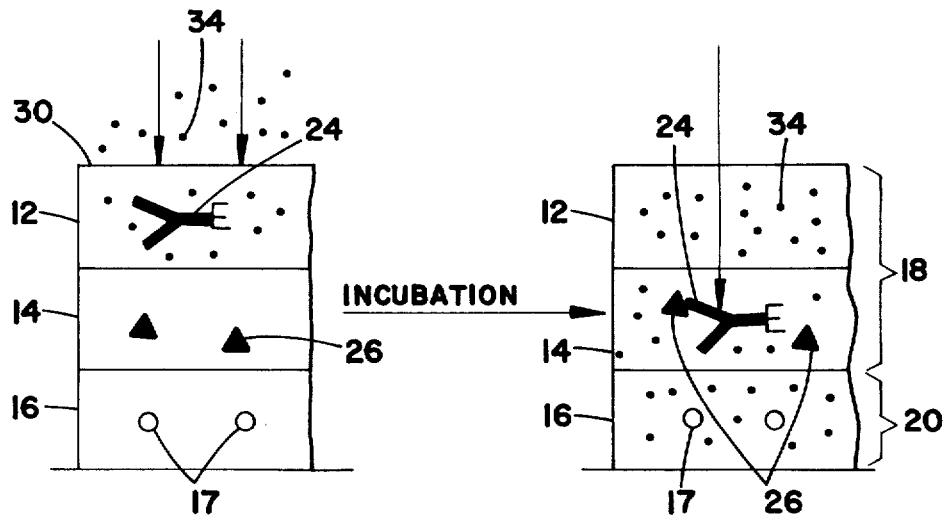
FIG. 3 is a diagrammatical illustration showing the method of the invention using the device of FIG. 1 and showing what happens when the test fluid is devoid of antigen. Specifically, a fluid, generally designated 34, is applied to the surface 30 of layer 12. As the fluid diffuses through layer 12 of the matrix, enzyme-linked antibodies 24 are solubilized and moved into layer 14 where they engage and become attached to bound antigens 26. Accordingly, no enzyme-linked antibodies reach the color forming reagent 17 in layer 16 (second zone 20) and no color change is observed. This of course, indicates that no antigens were present in the fluid 34.
Figure 4:
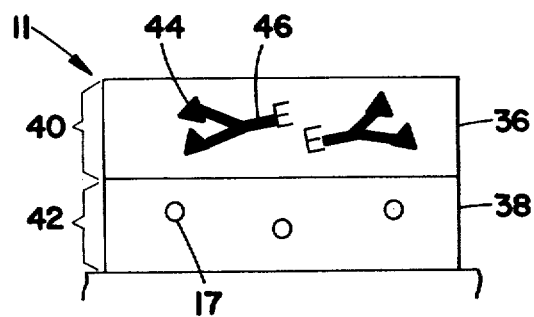
FIG. 4 shows an alternative embodiment of the invention wherein the device or matrix 11 is formed in two distinct layers 36 and 38. In this case, layer 36 is the first zone 40 having therein bound reference antigen 44 which is combined with enzyme-linked antibody 46. Layer 38 is the second zone 42 and contains color forming reagent 17.
Figure 5:
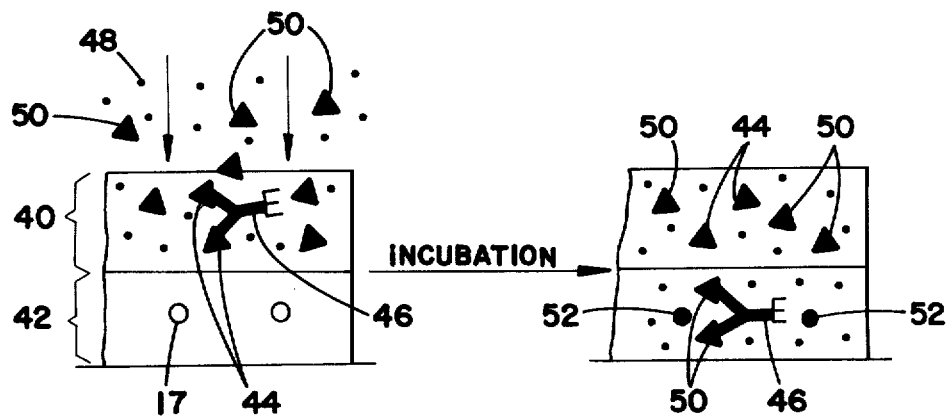
As shown in FIG. 5, when the test fluid 48 contains sufficient free antigen 50 to compete with the bound antigen 44, the enzyme-linked antibody will be displaced and will diffuse down into zone 42 to produce a color reaction 52.

In the preferred practice of the invention the immunoassay device is a sandwich of three, porous matrix layers (see FIG. 1). The first porous layer is impregnated with a specific antibody linked with an enzyme. The second porous layer contains immobilized (bound) reference antigen. The antigen is of the type specifically recognized by the antibody in the first porous layer. The third layer contains a color forming substrate which reacts with the enzyme linked to the antibody. The operation of the device is as follows (see FIGS. 2 and 3).

The fluid sample, containing the antigen to be tested, is placed in contact with the first layer. The free antigen in the test sample diffuses into the second layer and then into the third layer. The free antigen in the sample competes with the immobilized bound reference antigen in the second layer for combining with the enzyme-linked antibody. If the enzyme-linked antibody combines with free antigen, it will freely diffuse into the third layer and produce a color reaction. If the fluid sample contains no antigen, all the enzyme-linked antibody will have free binding sites and will combine with the immobilized antigen in the second layer. Enzyme-linked antibody which combines with the immobilized antigen in the second layer will not diffuse into the third layer, and no color reaction will be produced. The difference in the amount of substrate degraded (and intensity of color produced) is proportional to the amount of antigen in the test sample. For a given amount of enzyme-labeled antibody in the first layer, the sensitivity of the device is determined by the amount of reference antigen present in the second layer. Typically, a test device would contain a series of sandwich composites, each with a different amount of reference antigen. The series of reference antigen concentrations would have been previously determined to span a range of sensitivity, appropriate for the test solution being measured. It should be emphasized that in the ELISA test strip a positive color reaction indicates the presence of the antigen being tested.

The materials used to fabricate the device of the instant invention are well known in the art. However, in practice it has been found to be desirable to form the zones or layers of the preferred device from interwoven fibers such as nitrocellulose or diazobenzyloxymethyl (DBM) paper. Nitrocellulose paper directly binds proteins and has been shown to be useful for immobilizing antigens. DBM matrix binds DNA, RNA, and proteins by means of covalent linkages to the diazonium group. Additionally, a porous gel such as polyacrylamide, agarose, or collagen can be utilized. The antigen can be trapped within the pores of the gel, or it can be cross-linked to the gel via amino groups of the ligand and carboxylic groups on the matrix. Also, particles or beads containing the bound ligand trapped within a cellulose or plastic fiber matrix can be employed. A satisfactory example is polyacrylamide beads, 5–10 microns in diameter, with antigen bound to the surface via a peptide bond. The beads are trapped within a cellulose filter matrix of pore size 1–2 microns.

Suitable substrates or color-forming reagents are well known in the art. In this regard, a number of different types of purified enzymes are commonly labeled reagent for use in immunoassays such as ELISA. These include horseradish peroxidase, alkaline phosphatase, and beta-galactosidase. However, the present invention is not limited to the use of these enzymes to label the antibody or antigen. The enzyme used to label the antibody can produce a color in the second zone of the test device by acting directly or indirectly with the color forming agent. For example, substrates well known in the art such as diaminobenzidine or p-nitrophenylphosphate react with horseradish peroxidase in the presence of hydrogen peroxide to form a brown to black color. In one form of the present invention hydrogen peroxide is added exogeneously during the use of the device. Alternatively, the lyophilized color forming zone can contain bound glucose oxidase and the first zone can contain glucose. Upon use of the device, the glucose in the first zone diffuses into the second zone and generates hydrogen peroxide by reacting with glucose oxidase.

The enzyme linked to the antibody can produce a color in the second zone by an indirect means such as effecting the permeability of the zone. An example of this method found suitable for the present invention is the use of highly purified collagenase as the enzyme linked to the antibody. This enzyme degrades collagen into small peptides. To detect the collagenase label two reagents which combine to form a color are separated by a collagen matrix barrier. The presence of the collagenase labeled antibody is detected because the collagenase degrades the collagen barrier and allows the separated reagents to intermix and form a color. A suitable collagenase is that obtained from clostridium histolyticum purified by means well known in the art. A suitable collagen matrix is that formed by bovine type I collogen in triple helical (native) or denatured (gelatin) form.

The following are specific examples which further illustrate the practice of the instant invention.

EXAMPLE 1

TEST: Three Layer Embodiment Of The Invention For Pregnancy Detection

Materials Utilized a antigen: human chorionic gonadotrophin (hCG)
b antibody: rabbit antisera to human hCG
c enzyme linked to antibody: horseradish peroxidase
d color forming enzyme substrate: diamino benzidine
e matrix material forming porous layers: nitrocellulose.

Procedure:

Step 1. Preparation of layer containing color forming reagent: Nitrocellulose matrix sheets 0.2 mm thick were cut into strips 2 cm wide and 10 cm in length. The sheets were soaked for thirty minutes in a solution of 0.1 mg/ml diaminobenzidene in distilled water. The sheets were then frozen by covering them with dry ice pellets. The frozen sheets were lyophilized in a conventional lyophilizer.

Step 2. Preparation of antigen-containing layer: antigen was solubilized into phosphate buffered saline at a concentration of 5.0 I.U./ml, and made up as in a series of dilutions: 1:1, 1:2, 1:4, 1:8, 1:16, 1:32, 1:64 and 1:100.

Eight groups of nitrocellulose sheets were each soaked in a different dilution of the antigen solution for thirty minutes at 4° C. All sheets were then soaked in a solution of 1% bovine serum albumin in phosphate buffered saline for two hours at 4° C. to saturate all the free protein binding sites on the nitrocellulose. (Tobin et al. Proc. Natl. Acad. of Sci. 76 4350–4354, 1979.)

Step 3. Preparation of enzyme-linked antibody containing layer: Peroxidase enzyme was conjugated to the antibody by the standard periodate method of Wilson and Nakane (1978 in W. Knapp et al. (ed.) Immunofluorescence and Related Techniques, Elsevier Co., Amsterdam, p. 215–225). After purifying the conjugate by standard methods it was made up in PBS at a concentration of 1 mg/ml. The concentration of enzyme-linked antibody to be impregnated in the layer was determined by diluting the enzyme-linked antibody solution until a 20 microliter droplet applied to the surface of the nitrocellulose sheet containing immobilized antigen at a dilution of 1:32 showed complete binding of all the antibody to the immobilized antigen (preparation of a standard dilution curve). This concentration of enzyme-linked antibody was soaked into strips of cellulose blotter paper material and lyophilized as described for Step 1 above.

Step 4. Preparation of three-layer sandwich: 1 cm squares of each lyophilized layer were cut from the strips. The solid support was a strip of polycarbonate transparent plastic 10 cm × 1 cm × 0.1 mm thick. Eight squares of nirocellulose containing the color forming substrate were cemented to the plastic support with latex base cement. On top of these squares the antigen containing sheets were cemented using latex cement at the perimeter. The eight different antigen concentrations were used. Finally, on top of the antigen layers, the enzyme-linked antibody layers were glued.

Step 5. To perform the assay, fifty microliters of the test solution was applied to the surface of the top layer. The test solution consisted of standard antigen in phosphate buffered saline Ph 7.4 with 0.1% hydrogen peroxide. The sensitivity of the assay was 0.3 IU of hCG which exhibited a color reaction at the 1:32 dilution of immobilized antigen.

Results

The ELISA test strip fabricated as described above was compared for sensitivity to a standard hemagglutination reaction. The test sample was pooled human urine from six patients who were previously determined to be pregnant.

| DILUTION OF URINE SAMPLE | ESTIMATED hCG DETECTED | ELISA STRIP | CONVENTIONAL HEMAGGLUTINATION |
|---|---|---|---|
| 1:1 | 2.5 IU | (+) | (+) |
| 1:2 | 1.2 IU | (+) | (+) |
| 1:4 | 0.6 IU | (+) | (−) |
| 1:8 | 0.3 IU | (+) | (−) |
| 1:16 | 0.01 IU | (−) | (−) |

The sensitivity of the ELISA strip is greater than the conventional hemagglutination reaction.

EXAMPLE 2

TEST:
(a) To determine the time of color formation for various concentrations of enzyme-linked antibody impregnated into the first layer of the three layer embodiment.
(b) To determine the feasibility of detecting human hepatitis B antigen (HBA).

Procedure:

The test strip was constructed by methods identical to Example 1. The first layer contained lyophilized cellulose matrix impregnated with the following dilutions of peroxidase conjugated anti-HBA: ½, 1/5, 1/50, 1/225, 1/625, 1/3125. In experiment (a) the second layer contained no antigen. In experiment (b) the second layer contained bound HBA at a concentration of 500 nanograms per square cm. The third layer contained DAB substrate prepared as in Example 1 for detection of hCG.

RESULTS

Experiment (a)

The test sample consisted of normal human serum diluted 1/10 in phosphate buffered saline containing 0.1% hydrogen peroxide.

| Dilution of peroxidase conjugated anti-HBA in first layer | COLOR REACTION time | | |
|---|---|---|---|
| | 10 sec | 30 sec | 1 min |
| 1 | deep BN-BLK | same | same |
| 1/5 | deep BN-BLK | same | same |
| 1/50 | BN-BLK | same | same |
| 1/225 | BN | dark BN | same |
| 1/625 | light BN | BN | dark BN |
| 1/3125 | no color | very light BN | light BN |

KEY: BN = brown, BLK = black

Experiment (b).1

Determination of optimum maximal concentration of enzyme linked antibody in the first layer which is completely bound to the reference antigen in the second layer when the test sample is devoid of antigen.

| Dilution of Enzyme Conjugated Anti-HBA In First Layer | Color Reaction At One Minute |
|---|---|
| 1/5 | BN |
| 1/50 | light BN |
| 1/225 | very light BN |
| 1/625 | no color (complete binding by reference antigen) |
| 1/3125 | no color |

Conclusion:
The optimal concentration of enzyme-linked antibody is 1/625 when the second layer contains 500 nanograms of HBA per square cm. The feasibility of detecting HBA is demonstrated by the presence of competition of the free antigen for the bound reference antigen at 1/625.

Conclusion:

The optimal concentration of enzyme-linked antibody is 1/625 when the second layer contains 500 nanograms of HBA per square cm. The feasibility of detecting HBA is demonstrated by the presence of competition of the free antigen for the bound reference antigen at 1/625.

Experiment (b).2

A 1/625 dilution (from table (b)1 above of conjugate was chosen for detection of HBA at 100 nanograms/ml.

| Test Sample | Color Reaction | |
|---|---|---|
| | 30 sec | 1 min |
| HBA present | light BN | BN |
| HBA absent | no color | no color |

The technique of the present invention is equally applicable to both the detection of antibodies as well as antigens. The roles of the antigen and antibody would be simply reversed. For detecting antibodies, the antigen is labeled with enzyme and the reference antibody is immobilized in the first zone. The enzyme labeled antigen will bind to the immobilized antibody in the first zone in the absence of competing antibody in the test sample, and fail to diffuse into the second zone to form a color. If antibodies are present in the test sample they will compete with the immobilized reference antibodies. In this case a positive color reaction indicates the presence of antibodies in the test sample.

When the present invention is adapted to the detection of antibodies, a device is utilized which comprises a first zone containing enzyme-linked antigens and antibodies which are capable of immunologically reacting with said antigens, said antigens being positioned in said first zone such that they will be removed from said first zone when reacted with antibodies passing into or through said first zone but not removed from said first zone in the absence of such antibodies; and a second zone containing material capable of reacting, either directly or indirectly, with said enzyme-linked antigens to produce a color forming reaction which indicates the presence of said antigens.

While there have been described what are at present considered to be the preferred embodiments of this invention, it will be obvious to those skilled in the art that various changes and modifications may be made therein without departing from the invention, and it is, therefore, aimed in the appended claims to cover all such changes and modifications as fall within the true spirit and scope of the invention.

What is claimed is:

1. A device for determining the presence of antigens which comprises:
   a matrix;
   a first zone in said matrix containing (a) bound and immobilized antigens and (b) enzyme-linked antibodies which are capable of immunologically reacting with said antigens, said antibodies being positioned in said first zone such that they will be removed from said first zone when reacted with antigens passing through said first zone but not removed from said first zone in the absence of such antigens; and
   a second zone removed from said first zone containing material capable of reacting with said enzyme-linked antibodies to produce a color forming reaction which indicates the presence of said antibodies.

2. The device of claim 1 wherein said first and second zones are in a juxtapositioned relationship.

3. The device of claim 1 wherein said first zone contains enzyme-linked antibodies which are combined with bound and immobilized specific antigens.

4. The device of claim 1 wherein said first zone consists of at least two individual layers, with one of said layers containing enzyme-linked antibodies and another layer containing specific antigen bound and immobilized in said layer.

5. The device of claim 1 wherein said first zone is fabricated from nitrocellulose.

6. The device of claim 1 wherein said second zone is fabricated from nitrocellulose.

7. The device of claim 1 wherein said first zone is fabricated from a fibrous material.

8. The device of claim 1 wherein said second zone is fabricated from a fibrous material.

9. The device of claim 1 wherein said matrix is fabricated from a fibrous material.

10. The device of claim 9 wherein said fibrous material is diazobenzyloxymethyl paper.

11. The device of claim 1 wherein said first zone is fabricated from a porous polymer gel.

12. The device of claim 11 wherein said porous gel is at least one material selected from the group consisting of polyacrylamide, agarose and collagen gels.

13. A method for determining the presence of antigens in a biological fluid which comprises:
bringing a fluid which is to be tested for the presence of antigens into contact with a device having a matrix including a first zone containing (a) bound and immobilized antigens and (b) enzyme-linked antibodies which are capable of immunologically reacting with said antigens, said antibodies being positioned in said first zone such that they will be removed from said first zone but not removed from said first zone in the absence of such antigens, and a second zone removed from said first zone containing material capable of reacting with said enzyme-linked antibodies to produce a color forming reaction which indicates the presence of said antibodies;
allowing said fluid to permeate said device; and
observing the presence or absence of any color change in said second zone to thereby determine the presence or absence of the tested for antigen in said fluid.

14. The method of claim 13 wherein said first and second zones are in a juxtapositioned relationship.

15. The method of claim 13 wherein said first zone consists of at least two individual layers, with one of said layers containing enzyme-linked antibodies and another layer containing specific antigen bound and immobilized in said layer.

16. The method of claim 13 wherein said first zone consists of at least two individual layers, with one of said layers containing enzyme-linked antibodies and another layer containing specific antigen bound and immobilized in said layer.

17. The method of claim 13 wherein said first zone is fabricated from nitrocellulose.

18. The method of claim 13 wherein said second zone is fabricated from nitrocellulose.

19. The method of claim 13 wherein the antigen being determined is HCG and wherein the antigen in said device is human chorionic gonadatrophin.

20. The method of claim 13 wherein the antigen being determined is hepatitis antigen and wherein the antigen in said device is hepatitis antigen.

21. The method of claim 13 wherein the antigen being determined is rubella virus protein and wherein the antigen in said device is a rubella virus protein.

22. A device for determining the presence of antibodies which comprises:
a matrix;
a first zone is said matrix containing enzyme-linked antigens and bound and immobilized antibodies which are capable of immunologically reacting with said enzyme-linked antigens, said enzyme-linked antigens being positioned in said first zone such that they will be removed from said first zone but not removed from said first zone in the absence of such antibodies; and
a second zone removed from said first zone containing material capable of reacting with said enzyme-linked antigens to produce a color forming reaction which indicates the presence of said antigens.

23. A method for determining the presence of antibodies in a biological fluid which comprises:
bringing a fluid which is to be tested for the presence of antibodies into contact with a device having a matrix including a first zone containing enzyme-linked antigens and bound and immobilized antibodies which are capable of immunologically reacting with said enzyme-linked antigens, said enzyme-linked antigens being positioned in said first zone such that they will be removed from said first zone when reacted with antibodies passing through said first zone but not removed from said first zone in the absence of such antibodies, and a second zone removed from said first zone containing material capable of reacting with said enzyme-linked antigens to produce a color forming reaction which indicates the presence of said antigens;
allowing said fluid to permeate said device; and,
observing the presence of absence of any color change in said second zone to thereby determine the presence or absence of the tested for antibodies in said fluid.

* * * * *